US010632066B1

(12) United States Patent
Creasy, II et al.

(10) Patent No.: US 10,632,066 B1
(45) Date of Patent: Apr. 28, 2020

(54) METHOD OF PROVIDING BIRTH CONTROL

(71) Applicant: The Population Council, Inc., New York, NY (US)

(72) Inventors: George William Creasy, II, Glen Gardner, NJ (US); Ruth Beverly Merkatz, Rye, NY (US)

(73) Assignee: The Population Council, Inc., New York, NY (US)

(*) Notice: Subject to any disclaimer, the term of this patent is extended or adjusted under 35 U.S.C. 154(b) by 0 days.

(21) Appl. No.: 16/265,222

(22) Filed: Feb. 1, 2019

(51) Int. Cl.
*A61K 9/00* (2006.01)
*A61K 31/57* (2006.01)
*A61F 6/06* (2006.01)
*A61F 6/04* (2006.01)
*A61K 31/565* (2006.01)

(52) U.S. Cl.
CPC .............. *A61K 9/0036* (2013.01); *A61F 6/04* (2013.01); *A61F 6/065* (2013.01); *A61K 31/565* (2013.01); *A61K 31/57* (2013.01)

(58) Field of Classification Search
CPC .................................................... A61F 13/02
See application file for complete search history.

(56) References Cited

U.S. PATENT DOCUMENTS 5,989,581 A 11/1999 Groenewegen
9,296,780 B2 3/2016 Fuentes

FOREIGN PATENT DOCUMENTS

HU 0004967 A2 9/2002

OTHER PUBLICATIONS

Annovera® Product Information, Aug. 2018. (Year: 2018).*
NuvaRing® Center for Drug Evaluation and Research, Oct. 4, 2013 (Year: 2013).*
Crucitti et al., PLoS One. Jul. 23, 2018;13(7) (Year: 2018).*
Huang et al., PLos One 2015; 10(8), pp. 1-16. (Year: 2015).*
"ANNOVERA™: Highlights of Prescribing Information," TherapeauticsMD, Aug. 2018, 38 pages.
"Elcometrine—Population Council/Orion," Adis International Ltd., *Springer Nature Switerland AG*, Jan. 26, 2015, 11 pages.
"NuvaRing®: Highlights of Prescribing Information," Merck & Co., Oct. 2013, 36 pages.
"Safety and Efficacy of a Contraceptive Vaginal Ring Delivering Nesterone® and Ethinyl Estradiol," Population Council, https://clinicaltrials.gov/ct2/show/NCT00263341, first available online Dec. 8, 2005, 8 pages.
"Study of Efficacy, Cycle Control, and Safety of a NES-E2 Contraceptive Vaginal Ring," Population Council, https://clinicaltrials.gov/ct2/show/NCT03432416, first available online Feb. 14, 2018, 13 pages.

Archer, D. F., et al., "Impact of a One-Year Contraceptive Vaginal Ring Delivering Nestorone and Ethinyl Estradiol on Hepatic Estrogen-Sensitive Proteins," *Reproductive Sciences*, vol. 22(1): 111A-112A, Sage Journals, United States (2015).
Creasy, G., et al., "User controlled long acting reversible contraception: The pharmacokinetic profile of the Nestorone®/Ethinyl Estradiol Contraceptive Vaginal Ring(NES/EE-CVR) a 1-year Cyclical Re-useable Vaginal Ring," *The European Journal of Contraception and Reproductive Health Care*: S85, Taylor & Francis, United Kingdom (2014).
Edelman, A., et al., "A Novel Contraceptive Vaginal Ring Releasing Nestorone and Estradiol Dosed Continuously: Pharmacokinetics From a Dose Finding Study," *Fertility and Sterility* 108(3): e121, Elsevier, Netherlands (2017).
Fraser, I. S., et al., "Serum Nestorone® and ethinyl estradiol levels, and ovulation inhibition in women using three different dosage combinations of a Nestorone progestogen-ethinyl estradiol contraceptive vaginal ring on a bleeding-signaled regimen," *Contraception* 72: 40-45, Elsevier, Netherlands (2005).
Hoskin, E., et al., "Cycle control and bleeding patterns for a new contraceptive vaginal ring delivering 150 μg Nestorone® and 15 μg Ethinyl Estradiol: Results from a multi-centre, multi-national open label Phase 3 clinical trial," *The European Journal of Contraception and Reproductive Health Care*: S82-S83, Taylor & Francis, United States (2014).
Jensen, J. T., et al., "Use of Peak Drug Levels to Assess Compliance with Vaginal Ring Contraception," *ASRM Abstracts* 108(3): e12, Elsevier, Netherlands (2017).
Jensen, J. T., et al., "Continuous dosing of a novel contraceptive vaginal ring releasing Nestorone® and estradiol: pharmacokinetics from a dose-finding study," *Contraception* 97: 422-427, Elsevier, Netherlands, (2018).
Kumar, N., et al., "Nestorone® as a Novel Progestin for Nonoral Contraception: Structure-Activity Relationships and Brain Metabolism Studies," *Endocrinology* 158(1): 170-182, Oxford Academic, United Kingdom (2017).
Malcolm, K., et al., "Influence of silicone elastomer solubility and diffusivity on the in vitro release of drugs from intravaginal rings," *Journal of Controlled Release* 90: 217-225, Elsevier, Netherlands (2003).
Massai, M. R., et al., "Contraceptive efficacy and clinical performance of Nestorone implants in postpartum women," *Contraception* 64: 369-376, Elsevier, Netherlands (2001).
Merkatz, R., et al., "Preliminary results from a phase III study of the nestorone®/ethinyl estradiol contraceptive vaginal ring: a new, long acting (one year) user controlled contraceptive method," *The European Journal of Contraception and Reproductive Health Care: Abstracts of Free Communications*: FC-01, Taylor & Francis, United Kingdom (2010).

(Continued)

*Primary Examiner* — Jean P Cornet
(74) *Attorney, Agent, or Firm* — Sterne, Kessler, Goldstein & Fox, P.L.L.C.

(57) ABSTRACT

The present disclosure describes a vaginal system comprising segesterone acetate and ethinyl estradiol configured for thirteen 28-day product-use cycles that is compatible with male condoms comprising natural rubber latex, polyisoprene, or polyurethane and a method of providing birth control using the vaginal system wherein a secondary contraception is employed when the vaginal system is removed or expelled from the vagina for specified amounts of time during any of the product-use cycles.

11 Claims, 3 Drawing Sheets

(56) References Cited

OTHER PUBLICATIONS

Figure 1:
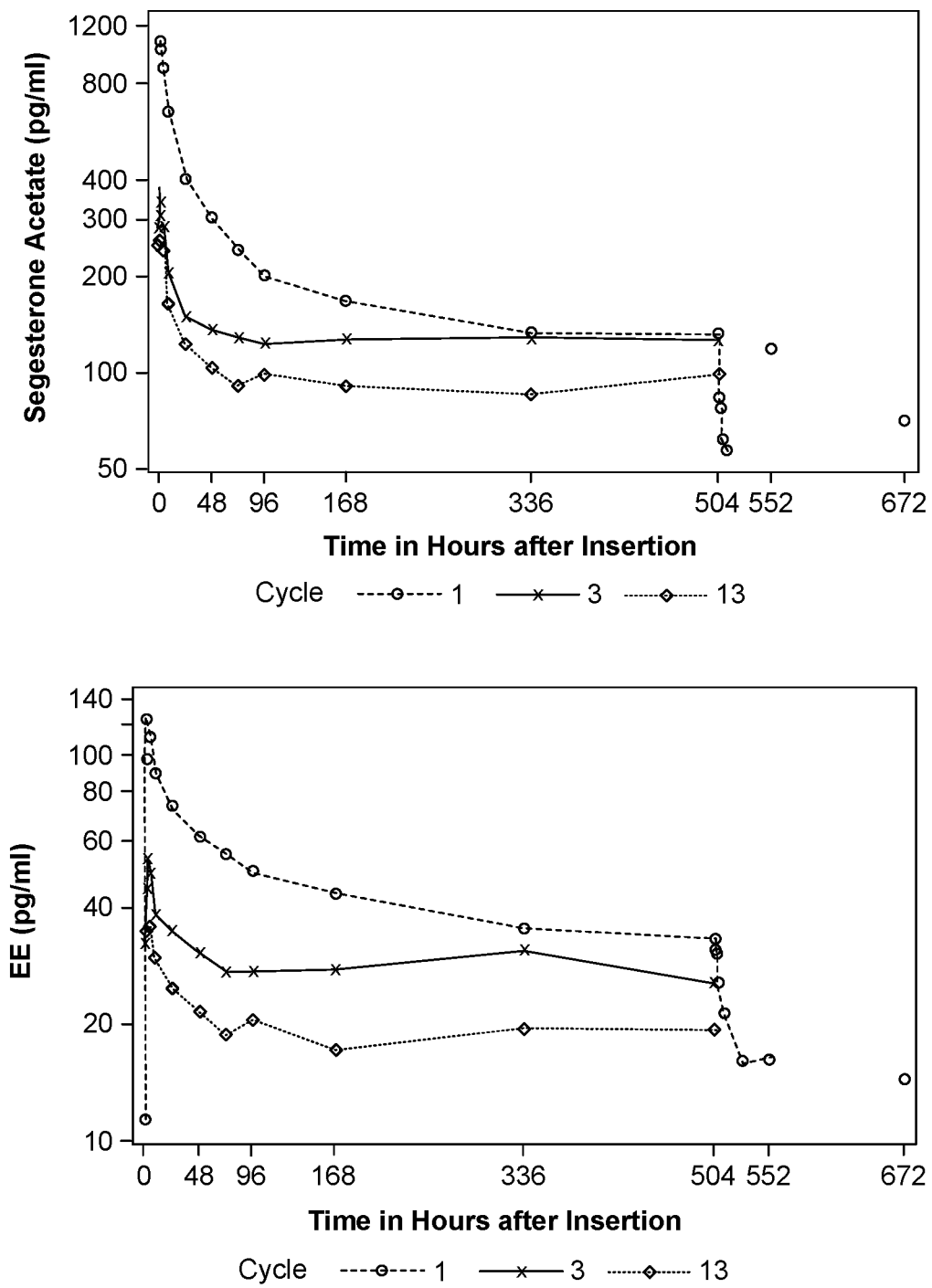

Merkatz, R., et al., "Efficacy, Safety and Acceptability of a New Contraceptive Vaginal Ring Delivering Nestorone (150 µg) and Ethinyl Estradiol (15 µg) Daily: Results From a Multi-Center Open Label Phase 3 Clinical Trial," *ASRM Abstracts* 100(3): S58, Taylor & Francis, United Kingdom (2013).

Merkatz, R., et al., "Efficacy, safety and acceptability of a new contraceptive vaginal ring delivering 150 µg Nestorone® and 15 µg Ethinyl Estradiol daily: Results from a multicenter open label Phase 3 clinical trial," *The European Journal of Contraception and Reproductive Health Care: Abstracts of Free Communications*:S67, Taylor & Francis, United Kingdom (2013).

Merkatz, R., et al., "Acceptability of the Nestorone®/Ethinyl Estradiol Contraceptive Vaginal Ring: Development of a Model; Implications for Introduction," *International Journal of Gynecology and Obstetrics* 131(5): E395-E396, Wiley Blackwell, United Kingdom (2015).

Merkatz, R., et al., "An acceptability model for the Nestorone®/Ethinyl Estradiol contraceptive vaginal ring," *The European Journal of Contraception and Reproductive Health Care* :S203-S204, Taylor & Francis, United Kingdom(2016).

Merkatz, R., et al., "Efficacy, Safety and Acceptability of a New Contraceptive Vaginal Ring Delivering Nestorone® 150 µg and Ethinyl Estradiol: Results From an Open Label Phase 3 Clinical Trial," *International Journal of Gynecology and Obstetrics* 131(5): E395, Wiley-Blackwell, United Kingdom (2015).

Merkatz, R., et al., "Development of the Nestorone®/Ethinyl Estradiol Contraceptive Vaginal Ring (NES/EE CVR); Challenges, Opportunities and Obligations of the Public Sector," *The European Journal of Contraception and Reproductive Health Care*: S192-S193, Taylor & Francis, United Kingdom (2016).

Mishell, D., et al., "Maximum Concentration and Exposure to Ethinyl Estradiol From the Nestorone®/Ethinyl Estradiol Contraceptive Vaginal Ring (NES/EE CVR)," *Reproductive Sciences* 22(1): 112A-113A, Sage Journals, United States (2015).

Rad, M., et al., "Comparative effects of a contraceptive vaginal ring delivering a nonandrogenic progestin and continuous ethinyl estradiol and a combined oral contraceptive containing levonorgestrel on hemostasis variables," *American Journal of Obstetrics and Gynecology* 195(1): 72-77, Elsevier, Netherlands (2006).

Rad, M., et al., "Effects of a contraceptive vaginal ring delivering nestorone® and ethinyl estradiol, and a combined oral contraceptive containing levonorgestrel, on markers of arterial disease," *Br. J. Clin. Pharmacol* 60(6): 677, Wiley Blackwell,United Kingdom (2005).

Robbins, A., et al., "Nestorone™ Progestin: The Ideal Progestin for Use in Controlled Release Delivery Systems," *Ann. N Y Acad. Sci* 828: 38-46, Wiley-Blackwell, United States (1997).

Sitruk-Ware, R., et al., "Nestorone®: clinical applications for contraception and HRT," *Steroids* 68: 907-913, Elsevier, Netherlands (2003).

Sitruk-Ware, R., et al., "A one-year contraceptive vaginal ring delivering Nestorone® and Ethinyl-Estradiol," *The European Journal of Contraception and Reproductive Health Care* :211, Taylor & Francis, United States (2014).

Sivin, I., et al., "Two-year performance of Nestorone®-releasing contraceptive implant: a three-center study of 300 women," *Contraception* 69: 137-144, Elsevier, Netherlands (2004).

Sivin, I., et al., "Contraceptive vaginal rings releasing Nestorone® and ethinylestradiol: a 1-year dose-finding trial," *Contraception* 71: 122-129, Elsevier, Netherlands (2005).

Stifani, B. M., et al., "Factors associated with nonadherence to instructions for using the Nestorone®/ethinyl estradiol contraceptive vaginal ring," *Contraception* 97: 415-421, Elsevier, Netherlands (2018).

Weisberg, E., et al., "Efficacy, Bleeding Patterns, and Side Effects of a 1-Year Contraceptive Vaginal Ring," *Contraception* 59: 311-318, Elsevier, Netherlands (1999).

McCoy, C. F., et al., "Solid state $^{13}$C NMR spectroscopy provides direct evidence for reaction between ethinyl estradiol and a silicone elastomer vaginal ring drug delivery system," *International Journal of Pharmaceutics* 548: 689-697, Elsevier, Netherlands (2018).

Merkatz, R. B., et al., "Acceptability of the nestorone®/ethinyl estradiol contraceptive vaginal ring: development of a model; implications for introduction," *Contraception* 90: 514-521, Elsevier, Netherlands (2014).

Sivin, I., et al., "Recent developments in contraceptive implants at the Population Council," *Contraception* 65: 113-119, Elsevier, Netherlands (2002).

Pheasant, R., "Polymorphism of 17-Ethinylestradiol," *J. Am. Chem. Soc.* 72: 4303-4304 (1950).

MED-1134 Safety Data Sheet, Date of Issue: Feb. 26, 2015.
MED-6385 Safety Data Sheet, Date of Issue: Feb. 14, 2014.
MED-6382 Safety Data Sheet, Date of Issue: Jan. 15, 2014.
MED-6381 Safety Data Sheet, Date of Issue: Jun. 26, 2014.
MED-6603 Safety Data Sheet, Date of Issue: Mar. 5, 2015.
MED-4870 Safety Data Sheet, Date of Issue: May 10, 2013.
MED4-4224 Safety Data Sheet, Date of Issuance: Jan. 6, 2015.
DDU-4320 Safety Data Sheet, Date of Issuance: Apr. 14, 2014.
Murphy, D. J. et al., "Controlling Levonorgesterel Binding and Release in a Multi-Purpose Prevention Technology Vaginal Ring Device," *J. Controlled Release* 226: 138-147 (2016).

Co-pending, U.S. Appl. No. 16/448,399, Inventor, Vairano, B., filed Jun. 21, 2019 (Not Published).

* cited by examiner

Mean Segesterone Acetate and Ethinyl Estradiol Serum Concentrations Delivered by ANNOVERA™ Over 21 Days of Dosing for Cycles 1, 3, and 13

Mean Segesterone Acetate and Ethinyl Estradiol Serum Concentrations Delivered by ANNOVERA™ Over the First 48 Hours of Dosing for Cycles 1, 3, and 13

| Schedule | | |
|---|---|---|
| Product-Use Cycle 1 | Put vaginal system in → (vaginal system change day) | Weeks 1, 2, and 3; Days 1-21 |
| | Day 1 | |
| | Take vaginal system out → (vaginal system change day) | Week 4 Days 22-28 |
| | Day 22 | |
| Product-Use Cycle 2 (repeat for Product-Use Cycles 3-13) | Put vaginal system in → (vaginal system change day) | Weeks 1, 2, and 3; Days 1-21 |
| | Day 1 | |
| | Take vaginal system out → (vaginal system change day) | Week 4 Days 22-28 |
| | Day 22 | |

FIG. 3

US 10,632,066 B1

METHOD OF PROVIDING BIRTH CONTROL

FIELD

This disclosure relates to a vaginal system comprising segesterone acetate and ethinyl estradiol configured for thirteen 28-day product-use cycles that is compatible with male condoms comprising natural rubber latex, polyisoprene, or polyurethane and a method of providing birth control using the system wherein secondary contraception is employed when the vaginal system is removed or expelled from a subject's vagina for specified amounts of time during any of the product-use cycles.

BACKGROUND

The use of oral contraception is widespread in the female population. But the need to remember a daily pill and the inconvenience of having to obtain frequent refills can reduce compliance, jeopardizing its effectiveness.

The use of subcutaneous upper arm implants and intrauterine devices (IUDs) as a means of administering contraception is seen as a way of overcoming these drawbacks as they remain effective for more than one year. These devices, however, have their own disadvantages as insertion and removal of implants and IUDs require a medical professional, such as a doctor, nurse, or physician's assistant.

Intravaginal rings are annularly shaped articles containing pharmaceutical agents (drugs) that can be introduced into the vagina in a simple manner without medical assistance. For example, NuvaRing® was designed to be used during single 28-day cycles. NuvaRing® is discarded at 21 days and a new ring inserted at the beginning of the next 28-day cycle. While the product provides a month of contraception without having to remember a daily pill, there is still a need for regular prescription refills during the year.

SUMMARY

The present disclosure provides a method of birth control that uses a vaginal system compatible with male condoms made from natural rubber latex, polyisoprene, or polyurethane and is configured for thirteen 28-day cycles wherein a secondary contraception product is employed when the vaginal system is removed or expelled from the vagina for specified amounts of time within any of the product-use cycles.

In one aspect, the present disclosure provides a method of preventing pregnancy in a female of reproductive potential, the method comprising: (a) reinserting into the vagina of a subject in need thereof, a natural rubber latex compatible, polyisoprene compatible, and polyurethane compatible vaginal system configured to release an average of approximately 0.15 mg/day of segesterone acetate and an average of approximately 0.013 mg/day of ethinyl estradiol in a 21-day first period in each of thirteen 28-day product-use cycles, following removal or expulsion of the vaginal system from the female's vagina for more than two cumulative hours during any 21-day first period in any of the thirteen 28-day product-use cycles; and (b) employing a secondary contraception product that does not comprise estrogen for seven days after reinserting the vaginal system.

In certain embodiments of this aspect, the removal or expulsion of the vaginal system from the female's vagina during any 21-day first period for more than two cumulative hours occurs in two or more instances on the same day, in two or more instances on consecutive or non-consecutive days, or via a combination of occurrences on the same and different days.

In additional embodiments of this aspect the secondary contraception product is a condom. In other embodiments the secondary contraception product is a male condom. In further embodiments the secondary contraception product is a female condom. In yet further embodiments the secondary contraception product is a hormonal contraception product.

In another aspect the present disclosure provides a method of providing birth control to a female of reproductive potential, the method comprising: (a) determining that a vaginal system comprising segesterone acetate and ethinyl estradiol configured to release an average of approximately 0.15 mg/day of segesterone acetate and an average of approximately 0.013 mg/day of ethinyl estradiol in a 21-day first period in each of thirteen 28-day product-use cycles, has been removed or expelled from the female's vagina for more than two cumulative hours during the 21-day first period; (b) reinserting the vaginal system; and (c) employing a secondary contraception product that does not comprise estrogen for seven days after reinserting the vaginal system; wherein the vaginal system is compatible with male condoms comprising natural rubber latex, polyisoprene, or polyurethane.

In another aspect the present disclosure provides a method of providing birth control to a female of reproductive potential, the method comprising inserting a vaginal system configured for thirteen 28-day product-use cycles into the female's vagina, wherein the vaginal system is compatible with male condoms comprising natural rubber latex, polyisoprene, or polyurethane, and wherein the vaginal system is configured to release an average of approximately 0.15 mg/day of segesterone acetate and an average of approximately 0.013 mg/day of ethinyl estradiol in a 21-day first period in each of thirteen 28-day product-use cycles; and wherein a secondary contraception product that does not comprise estrogen is employed when the vaginal system is removed or expelled from the female's vagina for more than two cumulative hours during a first period of any one of the thirteen 28-day product-use cycles.

In certain embodiments of this aspect the first period begins with an initial insertion of the system on either day 2, 3, 4, or 5 of the female's menstrual cycle.

In other embodiments each 28-day product-use cycle further comprises a second period during which the vaginal system is outside of the female's vagina, and wherein the second period begins with removal of the vaginal system on the day after the end of the first period.

In further embodiments the vaginal system is stored at room temperature during the second period.

In additional embodiments the method further comprises reinserting the vaginal system the day after the end of the second period, wherein the reinsertion occurs at approximately the same time of day as the initial insertion in the previous product-use cycle and wherein a secondary form of contraception that does not comprise estrogen is employed for seven days from the reinsertion when the system is reinserted more than 29 days after the previous product-use cycle's initial insertion.

In another aspect the present disclosure provides a method of birth control comprising: (a) initially inserting into the vagina of a female of reproductive potential a vaginal system configured for thirteen 28-day product-use cycles, wherein the system is compatible with male condoms comprising natural rubber latex, polyisoprene, or polyurethane, and wherein the system is configured to release an average of approximately 0.15 mg/day of segesterone acetate and an average of approximately 0.013 mg/day of ethinyl estradiol in a 21-day first period in each of the thirteen 28-day product-use cycles, wherein the initial insertion occurs on either day 2, 3, 4, or 5 of the female's menstrual cycle; (b) retaining the system in the patient's vagina for the first period of 21 days starting with and including the initial insertion date of step (a), wherein if the system is removed or expelled during the first period for more than two cumulative hours a secondary contraception product that does not comprise estrogen is employed; (c) removing the vaginal system on the day following the end of the first period; (d) storing the removed vaginal system for a second period of between five and seven days including the removal date of step (c), wherein the first and second period together comprise a product-use cycle; (e) repeating steps (a)-(d) for a total of up to thirteen product-use cycles including the first product-use cycle, wherein each initial insertion of step (a) is performed at approximately the same time of day as in the previous product-use cycle and wherein during any subsequent product-use cycle if the vaginal system is initially inserted more than 29 days after the previous initial insertion of step (a) a secondary contraception product that does not comprise estrogen is employed for seven days from the vaginal system reinsertion.

In other embodiments of this aspect the removed vaginal system is stored at room temperature.

BRIEF DESCRIPTION OF THE DRAWINGS/FIGURES

FIG. 1 depicts mean segesterone acetate and ethinyl estradiol serum concentrations delivered by the vaginal system over 21 days of dosing for cycles 1, 3, and 13.

Figure 2:
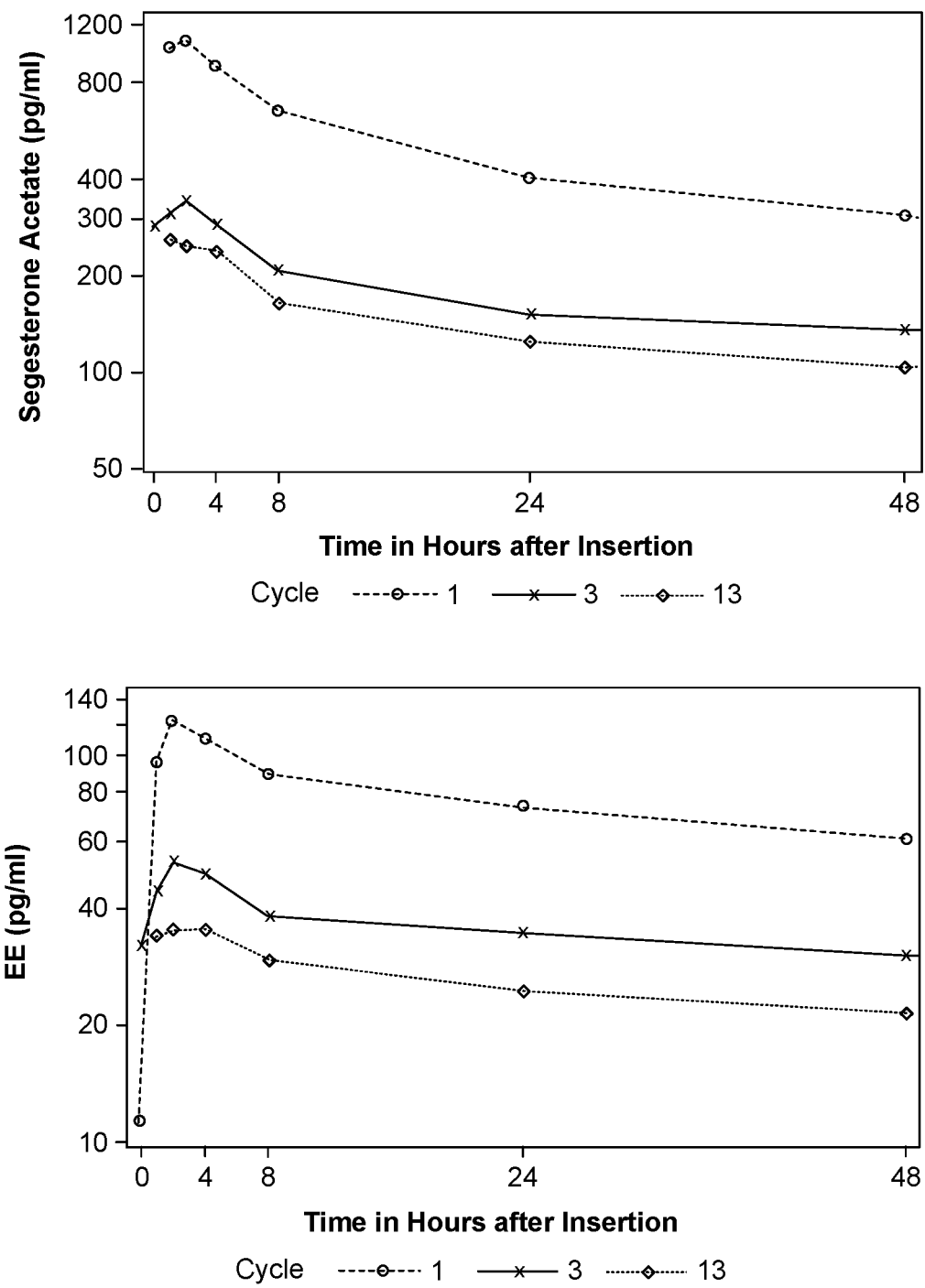

FIG. 2 depicts mean segesterone acetate and ethinyl estradiol serum concentrations delivered by the vaginal system over the first 48 hours of dosing for cycles 1, 3, and 13.

FIG. 3 is a graphical representation of a schedule for using the vaginal system described herein over 13 product-use cycles under normal use conditions.

DETAILED DESCRIPTION

The singular forms "a," "an," and "the" include plural referents unless the context dictates otherwise.

As used herein, the term "or" is a logical disjunction (i.e., and/or) and does not indicate an exclusive disjunction unless expressly indicated such as with the terms "either," "unless," "alternatively," and words of similar effect.

As used herein, the term "approximately" means ±10% of a noted value, unless otherwise specified.

The term "compatible" as used herein, refers to the ability of two or more items of different chemical makeup to come into repeated contact with each other over the course of an extended period of time, such as approximately 1 year, without a detrimental effect to any of the items coming into contact with each other over the period of time. Exemplary detrimental effects that do not occur when two or more items are compatible include, but are not limited to, a chemical reaction between the two or more items, an increase in brittleness in one or more of the items, tearing of one or more of the items, expansion or contraction of one or more of the items, breakage of one or more of the items, hardening of one or more of the items, softening of one or more of the items, erosion of one or more of the items, and/or reduced functionality of one or more of the items, such as a change in the rate of drug release from one of the items.

The phrase "two cumulative hours" as used herein, refers to multiple periods of time that together total 2 hours.

The term "day" as used herein, refers to a period of 24 hours.

"Ethinyl estradiol" and "EE" as used herein, refer to the compound with the established name 19-nor-17α-pregna-1,3,5(10)-trien-20-yne-3,17-diol, molecular formula $C_{20}H_{24}O_2$, having the structure:

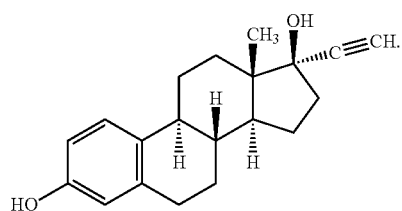

The physical form of the compound is a white to slightly yellowish-white crystalline powder. The compound is practically insoluble in water, freely soluble in alcohol, and dissolves in alkaline solution. Its melting point is 181° C.-185° C.

The phrase "first period" as used herein, refers to the 21 days that the vaginal system described herein is inside of a subject's vagina during a product-use cycle.

The phrase "initial insertion" as used herein, refers to the first insertion of the vaginal system into the vagina during a product-use cycle. In one embodiment of the present disclosure the initial insertion occurs on either day 2, 3, 4, or 5 of the female's menstrual cycle.

The terms "menstrual cycle" and "menstrual period" as used herein, refer to the process of ovulation and menstruation in women. In one embodiment of the present disclosure, day 1 is the first day of menstruation.

The phrase "natural rubber latex" as used herein, refers to the substance derived from the milky fluid obtained from plants such as the rubber tree.

The term "polyisoprene," as used herein, refers to a polymer of isoprene, the polymer having the structure:

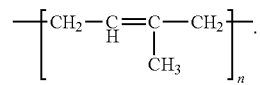

The term "polyurethane" as used herein, refers to a polymer composed of organic units joined by carbamate (urethane) links.

The phrase "product-use cycle" as used herein, refers to the combined number of days of the first period and the second period. In one embodiment of the present disclosure the product-use cycle of the vaginal system described herein is 28 days.

The terms "reinserting" and "reinsertion" as used herein, refer to any second or subsequent insertion of the vaginal system into the vagina within a given product-use cycle, and in particular, within the first period.

The term "reproductive potential" as used herein refers to the capacity for a female to produce offspring.

The phrase "room temperature" as used herein, refers to a temperature between 15° C. and 30° C.

The phrase "secondary contraception product" as used herein refers to a product other than the vaginal system described herein that provides birth control. In one embodiment of the present disclosure the secondary contraception product does not comprise estrogen.

The phrase "second period" as used herein, refers to the 5-7 days that the vaginal system is outside of a subject's vagina during a product-use cycle. The second period is a non-overlapping period immediately following the first period and is a "dose-free" interval. That is, the subject does not receive either SA or EE during this period.

"Segesterone acetate" and "SA" as used herein refer to the compound with the established name 16-methylene-17α-acetoxy-19-nor-pregn-4-ene-3,20-dione, molecular formula $C_{23}H_{30}O_4$, having the structure:

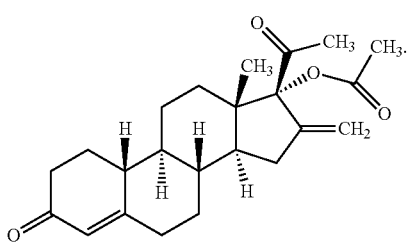

The physical form of the compound is a white, or yellowish white powder. The compound is slightly soluble in n-hexane, soluble in ethyl acetate and methanol, and freely soluble in acetone (USP classification). Segesterone acetate is sold under the trade name NESTORONE®.

The term "vaginal system" as used herein, refers to a device that is inserted into the vagina and prevents pregnancy. In one embodiment of the present disclosure the vaginal system comprises a vaginal ring. In another embodiment of the present disclosure the vaginal system comprises a progestin/estrogen combined hormonal contraceptive (CHC). In another embodiment of the present disclosure the vaginal system is a segesterone acetate and ethinyl estradiol system sold under the trade name ANNOVERA™.

In certain embodiments, the vaginal system of the present disclosure is a toroidal-shaped (i.e. ring-shaped), nonbiodegradable, flexible, opaque white, silicone elastomer that is 56 mm in overall diameter and 8.4 mm in cross-sectional diameter. In some embodiments, the elastomer can be a methyl siloxane-based polymer. In some embodiments, the vaginal system further comprises inactive ingredients including titanium dioxide, dibutyltin dilaurate, and silicone medical adhesive. In typical embodiments, each vaginal system is individually packaged in an aluminum pouch. Typically, the pouch consists of a laminate material comprising, from outside to inside, polyester, aluminum foil, and polyethylene. A black compact case can be provided for storage of the system by patients.

In typical embodiments, the vaginal system is not made with natural rubber latex. In some embodiments, it contains two channels of approximately 3.0 mm diameter and 27 mm length into which steroid-containing cores are inserted.

In some embodiments, the vaginal system contains 103 mg of SA distributed throughout both cores and 17.4 mg of EE distributed throughout only one core. In some embodiments, one of the cores contains 40% SA and 12% EE by mass and is 3 mm in diameter and 18 mm in length and releases both SA and EE. In some embodiments, the other core contains 50% SA by mass and is 3 mm in diameter and 11 mm in length and releases SA alone. In some embodiments, contact between the cores and the vaginal system body can be fixed by coating the channels with silicone medical adhesive before introducing the cores. After insertion of the cores, the channels can be sealed with additional silicone medical adhesive.

In embodiments where the system contains 103 mg SA and 17.4 mg EE, the system can release an approximate average 0.15 mg/day of SA and 0.013 mg/day of EE when placed in the vagina over a period of 21 days of each product-use cycle for up to 13 product-use cycles (total of 273 days). Each product-use cycle is 28 days and comprises a first period of 21 days and a second period of 7 days. Typically, the vaginal system is self-inserted by the subject into the vagina for the first period and is removed for the second period. The day of the week when the vaginal system is inserted for the first time in the first period, i.e. day 1, is the vaginal system change day. The day of the week when the vaginal system is removed for the beginning of the second period, i.e. day 22, is likewise referred to as the vaginal system change day. This cycle is shown visually in FIG. 3. Each vaginal system is designed to be used for up to 13 product-use cycles (1 year), before being discarded.

Although the vaginal system provides SA and EE in the approximate rates described above, SA and EE can diffuse out of the vaginal system with release rates that vary over time. In certain embodiments, the daily in vitro release rates of SA and EE are higher during each initial 24-48 hours of use in a given product-use cycle, achieving a somewhat lower steady-state with continued use over subsequent days in each product-use cycle. Based on the residual amount of drug in vaginal systems used in clinical trials over 13 product-use cycles, a total of approximately 41.3 mg of SA and approximately 3.4 mg of EE are released over this period.

When used by a subject of reproductive potential, one system should be placed in the subject's vagina. In certain embodiments, and for maximum contraceptive effectiveness, the vaginal system can remain in the vagina continuously for 21 days (3 complete weeks), i.e. the first period. Upon completion of the first period, the vaginal system should be removed for the second period which, in typical embodiments, is one week. During the second period, a withdrawal bleed usually occurs. Once removed, the vaginal system should be cleaned with mild soap and warm water, patted dry with a clean cloth towel or paper towel, and placed in its case for the duration of the second period. At the end of the second period, the vaginal system should be cleaned prior to being placed back in the vagina for another first period of 21 continuous days (3 complete weeks). In preferred embodiments, this product-use cycle can be repeated and can provide contraception for 13 product-use cycles.

The vaginal system can be inserted using a variety of techniques. For example, the user can choose an insertion position that is comfortable, such as lying down, squatting, or standing. Typically, the sides of the vaginal system can be pressed together for insertion into a subject's vagina. When properly inserted, the vaginal system should be entirely in the vagina and behind the pelvic bone. The day and time of insertion should be noted so that the vaginal system can be removed 3 weeks later on the same day and at about the same time, i.e. at the end of the first period.

The system can be removed by hooking an index finger into the vaginal system inside the vagina and gently pulling the vaginal system.

After 13 product-use cycles, and because the vaginal system still contains both SA and EE, the system should be placed in the case that comes with it and disposed of at a drug take-back location, if available. If a drug take-back location is not available, it should be disposed of in the trash.

Beginning Use of the Vaginal System

If hormonal birth control is not being used (and if any copper IUD has been removed), the vaginal system should be started between days 2 and 5 of the menstrual period. If menstrual periods are not regular or if the system is started more than 5 days from the start of the menstrual period, a barrier method of birth control, such as a male condom or spermicide, should be used during sexual intercourse for the first 7 days that the vaginal system is used.

If changing from a birth control pill or patch or monthly disposable contraceptive vaginal ring to the vaginal system described herein, and the previous method has been used correctly and there is no possibility of pregnancy, a change to the system described herein can occur any day of the birth control cycle without the need for backup contraception. The vaginal system described herein cannot be started any later than the start date of the next birth control pill, the application date of the next patch, or the insertion date of the next monthly disposable contraceptive vaginal ring. No more than 7 hormone-free days should occur before starting the system.

If switching from a minipill, injection, implant, or an intrauterine system (i.e., Progestin-Only Method [Progestin-only pills (POP), Progestin Injection, Progestin Implant, Progestin Intrauterine System (IUS)] to the vaginal system described herein, and there are no contraindications to the use of EE, the switch can be made from a progestin-only method to the present system. If switching from progestin-only pills, the vaginal system should start at the time the next POP pill would have been taken. If switching from an injection, the vaginal system described herein should be started at the time of the next scheduled injection. If switching from an implant or an IUS, the system should be started at the time of implant or IUS removal. In all of these cases an additional barrier method, such as a male condom or spermicide, should be used during coitus for the first 7 days of use of the system.

If there are no contraindications to the use of EE, the vaginal system described herein may be initiated for contraception within the first 5 days following a complete first trimester abortion or miscarriage without additional back-up contraception. If more than 5 days have elapsed from the first trimester abortion or miscarriage, a non-hormonal birth control method, such as male condoms or spermicide, should be used while waiting for the next menstrual period to start. The vaginal system should then be started between days 2 and 5 of the menstrual period. If the system is started more than 5 days from the start of the menstrual period, a barrier method of birth control, such as a male condom or spermicide, should be used during sexual intercourse for the first 7 days that the system is used.

The vaginal system described herein should not be started earlier than 4 weeks (28 days) after a second trimester abortion or miscarriage (after the first 12 weeks of pregnancy) due to the increased risk of thromboembolism.

The vaginal system described herein should not be started sooner than 4 weeks postpartum and should only be started in subjects who choose not to breastfeed. Prior to 4 weeks postpartum there is an increased risk of thromboembolism. If the system is started 4 or more weeks after having a baby and a menstrual period has not started, another method of birth control should be used until the system has been used for 7 days in a row. The possibility of ovulation and conception occurring should be considered prior to initiating use of the vaginal system described herein.

Breastfeeding women should not use the vaginal system described herein. Females who are breastfeeding should use other birth control methods and not use the system until after weaning.

When the vaginal system described herein is being used, regular 28-day cycles should be expected. Bleeding or spotting may occur between scheduled periods, especially during the first product-use cycle. If spotting continues for more than 7 consecutive days a health care provider should be consulted. If a period does not occur, a health care provider should be consulted. If pregnancy is confirmed by a health care provider, the vaginal system use should be discontinued. However, the system should not be removed until pregnancy is confirmed.

Deviation from Intended Use

Contraceptive efficacy of the vaginal system may be reduced if the subject deviates from the recommended use. The system should remain in the vagina for the first period, i.e. 21 days (3 weeks) and then it should be taken out of the vagina for 7 days. In a 28-day product-use cycle, comprising a first period and a second period, a deviation that involves the system being out of the vagina for less than 7 days during the second period will not increase pregnancy risk, but a deviation that involves the system being out of the vagina for more than 7 days during the second period will increase pregnancy risk and back-up contraception is recommended in these instances. Deviations from the recommended regimen may result in a new vaginal system change day.

If the vaginal system is removed too soon or is reinserted too late, the chance of getting pregnant is higher. For example, if the subject is 1 or 2 days off schedule (late) for vaginal system insertion or reinsertion, a new vaginal system-in and vaginal system-out day will need to be recorded for the remaining product-use cycles. Back-up contraception, such as condoms or spermicide, will also have to be used for the first 7 days of the new schedule. If the system is out for only 5 or 6 days, it should stay in for at least 3 weeks (21 days). It may be retained until the scheduled vaginal system-out day. If the system is reinserted after being out for more than 7 days, it should be immediately inserted and a new vaginal system in-day recorded. Condoms or spermicide should be used as back-up contraception for a period of 7 days. If the vaginal system is removed after being in for only 19 or 20 days, it should be left out for a week, then reinserted and retained to the normal vaginal system-out day, 22 or 23 days after the vaginal system was inserted or reinserted. If the system is removed after 22 or 23 days, it should be immediately removed and then reinserted 7 days later.

Although the vaginal system described herein is extremely effective, it has been surprisingly discovered that it is appropriate to use back-up or secondary contraception such as male condoms or spermicide when the vaginal system is out of the vagina for more than 2 continuous hours or more than 2 cumulative hours during the first period. In such situations back-up contraception should be used until the vaginal system has been in the vagina for 7 consecutive days.

Deviation from intended use can be intentional or unintentional. For example, the vaginal system can be removed for repositioning, to increase comfort during coitus, or for any other reason. Likewise, it can be unintentionally expelled, such as while removing a tampon, during coitus, or with straining during a bowel movement. If the vaginal system is intentionally removed or unintentionally expelled once during the 21 days of intravaginal use and is replaced within 2 hours, contraceptive efficacy should not be reduced and no back-up contraception is needed. In instances where the vaginal system is accidently or unintentionally expelled, it should be washed with mild soap and warm water, rinsed and patted dry with a clean cloth towel or paper towel, and replaced as soon as possible.

Alternatively, when the system is out of the vagina for more than 2 continuous hours or more than 2 cumulative hours during the first period, then back-up contraception, such as male condoms or spermicide, should be used until the vaginal system has been in the vagina for 7 consecutive days. The use of combined hormonal contraceptives (those containing an estrogen) for emergency contraception during use of the vaginal system described herein is not recommended.

The period of time exceeding two cumulative hours can be arrived at via a number of combinations of intentional and unintentional removals or expulsions of the vaginal system from a subject's vagina. In certain embodiments, however, the time exceeding two cumulative hours can be achieved via 2, 3, 4, 5, or more instances where the vaginal system is removed or expelled from the subject's vagina. In certain embodiments, each instance where the vaginal system is removed or expelled can take place on a different consecutive or non-consecutive day within the 21-day first period, such that the period of time exceeding two cumulative hours will only be reached after several days. In other embodiments, some instances of removal or expulsion can take place on the same day, while others take place on different consecutive or non-consecutive days within the 21-day first period. In still other embodiments, each instance where the vaginal system is removed or expelled from the subject's vagina can occur on the same day, such that the period of time greater than two cumulative hours will be reached in a single day. In each case, however, the period of time greater than two cumulative hours will be reached via two or more instances where the vaginal system is removed or expelled from the subject's vagina.

More specifically, and by way of example only, where the vaginal system is intentionally removed for 90 minutes on a first day during the first period, and unintentionally removed or expelled for 90 minutes on a second consecutive or non-consecutive day during the first period, (total cumulative time out during the first period=3.0 hours), back-up contraception should be used for seven consecutive days following reinsertion of the system after the second 90 minute removal. The preceding example is meant as an example only and many other possible combinations of intentional and unintentional vaginal system removal during the first period, each for varying durations of time, are possible and considered to be within the scope of this disclosure.

Monitoring deviation and determining whether the vaginal system has been removed or expelled from the vagina for more than two cumulative hours during any first period can be performed in numerous ways. For instance, the subject using the vaginal system can keep a journal (either in paper or electronic format) to monitor the total time that the vaginal system has been out of the body during any of the 21-day first periods. Alternatively, the subject can keep track of the cumulative time out of the body during any of the first periods mentally. Other methods of keeping track of the vaginal system's time out of the vagina and determining whether the vaginal system has been removed or expelled for more than two cumulative hours are known and within the skill of the ordinarily skilled artisan in view of this disclosure.

Despite the need for secondary or back-up contraception when the vaginal system has been removed or expelled for more than two cumulative hours during the first period, it has further been surprisingly discovered that the vaginal system is compatible with condoms (male or female) made from natural rubber latex, polyurethane, and polyisoprene. That is, when the vaginal system is repeatedly exposed to a condom comprising the various polymers noted above over one or more of the thirteen product-use cycles, there is no concern that the system's efficacy will decrease as a result of this exposure, or conversely, that the system will have a negative impact on the condom. More specifically, contacting the vaginal system with one or more condoms over a product-use cycle will not cause or increase oxidative degradation of the vaginal system or the condom, cause or increase thermal degradation of the vaginal system or the condom, increase or decrease drug delivery rates from the vaginal system, cause or increase hydrolysis in the vaginal system or condom, or otherwise cause an unwanted reaction or side effect as a result of the interaction.

This compatibility is advantageous not only when using condoms as a secondary/backup form of birth control when needed, but also when using condoms as a means to prevent the transmission of sexually transmitted infections because the vaginal system described herein does not protect against HIV-infection (AIDS) and other sexually transmitted infections.

Prolonged Vaginal System Free Interval

If the Vaginal System Free Interval is prolonged, the possibility of pregnancy should be considered and the female should use back-up contraception, such as male condoms or spermicide, during coitus until the vaginal system has been in the vagina for 7 consecutive days. The use of combined hormonal contraceptives (those containing an estrogen) for emergency contraception during use of the vaginal system described herein is not recommended.

Prolonged Use of the System

If the vaginal system is left in the vagina for more than 21 days, it should be removed for 7 days and then reinserted for 21 days to resume a 21/7 schedule. The vaginal system described herein has not been adequately evaluated in females with a body mass index of >29 kg/m2. This subpopulation was excluded from the clinical trials after two venous thromboembolisms (VTEs) occurred in this group. Higher body weight associates with lower systemic exposure of SA and EE. In a PK study conducted in 18 females with BMI<25 (16.89-24.34) kg/m$^2$ and 21 females with BMI>25 (25.15-37.46) kg/m$^2$, up to 16% and 33% decreases in the systemic exposure ($AUC_{0-21day}$) of SA and EE, respectively, were observed between the two BMI groups.

The vaginal system described herein is contraindicated for females with a high risk of arterial or venous thrombotic diseases. Examples include females over the age of 35 who smoke, females who have or have a history of deep vein thrombosis or pulmonary embolism, females who have cerebrovascular disease, females who have coronary artery disease. In addition, the vaginal system is contraindicated in females who have thrombogenic valvular or thrombogenic rhythm disease of the heart (for example, subacute bacterial endocarditis with valvular disease, or atrial fibrillation). The vaginal system described herein is also contraindicated in females who have inherited or acquired hypercoagulopathies. The system should be discontinued immediately if there is unexplained loss of vision, proptosis, diplopia, papilledema, or retinal vascular lesions and evaluate for retinal vein thrombosis.

The vaginal system described herein is contraindicated in females who have or have a history of breast cancer or other estrogen- or progestin-sensitive cancer, for females who have liver tumors, acute hepatitis, or severe (decompensated) cirrhosis, for females who have undiagnosed abnormal uterine bleeding, for females who have a hypersensitivity to any of the components of the system and for females who use Hepatitis C drug combinations containing ombitasvir/paritaprevir/ritonavir, with or without dasabuvir. The system can be restarted 2 weeks following completion of this regimen. Use of the vaginal system described herein should be stopped if a thrombotic or thromboembolic event occurs. The system should be stopped at least 4 weeks before and through 2 weeks after major surgery or other surgeries known to have an elevated risk of VTE Cardiovascular risk factors should be considered before initiating in all females, particularly those over 35 years. The system should not be used by females with uncontrolled hypertension or hypertension with vascular disease. If used in females with well-controlled hypertension, blood pressure should be monitored and use of the system discontinued if blood pressure rises significantly.

The vaginal system described herein is contraindicated in females with acute hepatitis or severe (decompensated) cirrhosis of the liver. It should be discontinued if jaundice occurs. Acute liver test abnormalities may necessitate the discontinuation use until the liver tests return to normal and system causation has been excluded.

Glucose should be monitored in prediabetic and diabetic females taking the vaginal system described herein. An alternate contraceptive method should be considered for females with uncontrolled dyslipidemias. The system is contraindicated for females with diabetes mellitus who are over age 35, females who have diabetes mellitus with hypertension or vascular disease, who have other end-organ damage, or who have diabetes mellitus of >20 years duration. Females with hypertriglyceridemia, or a family history thereof, may be at an increased risk of pancreatitis when using the system.

Significant change in headaches should be evaluated and use of the system discontinued if indicated. The vaginal system is contraindicated in females who have headaches with focal neurological symptoms, who have migraine headaches with aura, or who are over age 35 with any migraine headaches.

The vaginal system described herein may cause irregular bleeding or amenorrhea. Bleeding/spotting that occurs during the dose-free week when the vaginal system is out is considered "scheduled" bleeding. Bleeding and/or spotting that occurs at any time while the vaginal system is inserted is considered "unscheduled" bleeding/spotting. If these persist, other causes should evaluated.

The most common adverse reactions (>5%) are headache/migraine, nausea/vomiting, vulvovaginal mycotic infection/candidiasis, abdominal pain lower/upper, dysmenorrhea, vaginal discharge, urinary tract infection, breast tenderness/pain/discomfort, bleeding irregularities including metrorrhagia, diarrhea, genital pruritus. Serious adverse reactions occurring in ≥2 subjects were: VTEs (deep venous thrombosis, cerebral vein thrombosis, pulmonary embolism); psychiatric events; drug hypersensitivity reactions; and spontaneous abortions.

Drugs or herbal products that induce certain enzymes, including CYP3A4, may decrease the effectiveness of the system or increase breakthrough bleeding. Examples of incompatible drugs and herbal products include, but are not limited to, apreppitant, barbiturates, bosentan, carbamazepine, efavirenz, felbamate, griseofulvin, oxcarbazepine, phenytoin, rifampin, rifabutin, rufinamide, topiramate, products containing St. John's wart, and certain protease inhibitors. Back-up or alternative method of contraception should be used when enzyme inducers are used with the system. Continue back-up contraception for 28 days after discontinuing the enzyme inducer to maintain contraceptive reliability.

Co-administration of atorvastatin or rosuvastatin and certain CHCs containing EE increase systemic exposure of EE by approximately 20-25%. Ascorbic acid and acetaminophen may increase plasma EE concentrations, possibly by inhibition of conjugation. CYP3A4 inhibitors such as itraconazole, voriconazole, fluconazole, grapefruit juice, or ketoconazole may increase systemic exposure of the estrogen and/or progestin component of the system.

Significant decreases in systemic exposure of estrogen and/or progestin have been noted when CHCs are co-administered with some HIV protease inhibitors (e.g., nelfinavir, ritonavir, darunavir/ritonavir, (fos)amprenavir/ritonavir, lopinavir/ritonavir, and tipranavir/ritonavir), some HCV protease inhibitors (e.g., boceprevir and telaprevir), and some non-nucleoside reverse transcriptase inhibitors (e.g., nevirapine). In contrast, significant increases in systemic exposure of estrogen and/or progestin have been noted when CHCs are co-administered with certain other HIV protease inhibitors (e.g., indinavir and atazanavir/ritonavir) and with other non-nucleoside reverse transcriptase inhibitors (e.g., etravirine).

Concomitant use of CHCs with lamotrigine may significantly decrease systemic exposure of lamotrigine due to induction of lamotrigine glucuronidation. Decreased systemic exposure of lamotrigine may reduce seizure control. Dose adjustment for lamotrigine may be necessary. Product labeling for lamotrigine should be consulted.

Concomitant use of CHCs with thyroid hormone replacement therapy or corticosteroid replacement therapy may increase systemic exposure of thyroid-binding and cortisol-binding globulin. The dose of replacement thyroid hormone or cortisol therapy may need to be increased. Approved product labeling for the therapy in use should be consulted.

Concomitant use of CHCs may decrease systemic exposure of acetaminophen, morphine, salicylic acid, and temazepam. Concomitant use with ethinyl estradiol containing CHCs may increase systemic exposure of other drugs (e.g., cyclosporine, prednisolone, theophylline, tizanidine, and voriconazole). The dosage of drugs that can be affected by this interaction may need to be increased or decreased. The approved product labeling for the concomitantly used drug should be consulted.

In a drug-drug interaction study with the vaginal system described herein and the concurrent use of three different formulations of vaginal miconazole, the use of water-based vaginal miconazole cream resulted in no change in exposure to EE or SA from the vaginal system. However, the use of either the 1 day or the 3-day oil-based miconazole suppository was associated with an overall increase in exposure up to 67% for EE and 32% for SA. Considering the potential long-term effect on vaginal system performance, concurrent use of oil-based vaginal suppositories should not occur with the system's use. If there is a need to treat a vaginal condition, water-based vaginal cream or oral therapy may be used concurrently with the vaginal system.

Water-based vaginal lubricants have no effect on the vaginal system described herein; however, oil-based (including silicone-based) vaginal lubricants will alter the vaginal system and/or exposure to EE and SA and should not be used.

The effect of tampon use on the systemic exposure of SA and EE from the vaginal system described herein has not been studied.

The use of contraceptive steroids may influence the results of certain laboratory tests, such as coagulation factors, lipids, glucose tolerance, and binding proteins.

Females with a history of depression should be monitored and the system should be discontinued if depression recurs to a serious degree.

The estrogen component of the vaginal system described herein may raise the serum concentrations of thyroxine-binding globulin, sex hormone-binding globulin, and cortisol-binding globulin. The dose of replacement thyroid hormone or cortisol therapy may need to be increased.

In females with hereditary angioedema, exogenous estrogens may induce or exacerbate symptoms of angioedema.

Chloasma may occur with use of the vaginal system described herein, especially in females with a history of chloasma gravidarum. Females who tend to develop chloasma should avoid exposure to the sun or ultraviolet radiation while using the system.

Cases of toxic shock syndrome (TSS) have been reported by vaginal ring users. TSS has been associated with tampons and certain barrier contraceptives, and in some TSS cases ring users were also using tampons. Causal relationship between the use of a vaginal ring and TSS has not been established. No cases of TSS occurred in clinical trials with use of the vaginal system described herein. If a female exhibits signs or symptoms of TSS, the possibility of this diagnosis should be considered and the vaginal system should be removed. Appropriate medical evaluation and treatment should be initiated.

Some females are aware of the vaginal system on occasion during the 21 days of use or during coitus, and partners may feel the vaginal system during coitus.

The vaginal system described herein may not be suitable for females with conditions that make the vagina more susceptible to vaginal irritation or ulceration. Vaginal and cervical erosion and/or ulceration has been reported in females using other contraceptive vaginal devices. In some cases, the ring adhered to vaginal tissue, which necessitated removal by a health-care provider.

Epidemiologic studies and meta-analyses have not found an increased risk of genital or nongenital birth defects (including cardiac anomalies and limb-reduction defects) following exposure to CHCs before conception or during early pregnancy. In the U.S. general population, the estimated background risk of major birth defects and miscarriage in clinically recognized pregnancies is 2-4% and 15-20%, respectively. The vaginal system described herein should be discontinued if pregnancy occurs, because there is no reason to use CHCs during pregnancy. No studies have been conducted of the use of the system in pregnant females.

No studies were conducted in subjects with renal impairment; the vaginal system described herein is not recommended in patients with renal impairment.

There have been no reports of serious ill effects from overdose of CHCs. Overdosage may cause withdrawal bleeding in females and nausea. In case of suspected overdose, all vaginal systems should be removed and symptomatic treatment given.

Carcinogenesis

In a 2-year carcinogenicity study in rats with subdermal implants releasing 40, 100, and 200 µg segesterone acetate per day (approximately 17-86 times the daily dose of segesterone acetate in females using the system based on body surface area), no drug-related increase in tumor incidence was observed. In a 2-year intravaginal carcinogenicity study in mice, segesterone acetate gel produced an increased incidence of adenocarcinoma and lobular hyperplasia in the breast at a dose of 30 mg/kg/day, approximately 10 times the systemic exposure of segesterone acetate per day in females using the system described herein based on AUC. A dose of 10 mg/kg/day in the mouse, approximately 3 times the systemic exposure of segesterone acetate per day based on AUC, did not result in carcinogenic findings. Long-term continuous administration of natural and synthetic estrogens in certain animal species increases the frequency of carcinomas of the breast, uterus, cervix, vagina, testis, and liver.

Mutagenesis

Segesterone acetate was neither mutagenic nor clastogenic in the Ames/*Salmonella* reverse mutation assay, the chromosomal aberration assay in Chinese hamster ovary cells, or in the in vivo mouse micronucleus test.

Impairment of Fertility

A return to fertility study was conducted with segesterone acetate in rats, using subdermal implants releasing a dose approximately 25 times the anticipated daily vaginal human dose (based on body surface area). Three months of treatment with segesterone acetate suppressed fertility, but 7 weeks after cessation of treatment, there were no adverse effects on ovulation or resulting litter parameters.

Resumption of fertility after discontinuation of the vaginal system described herein is expected. All women followed for return of fertility experienced a return of fertility by 6 months after discontinuing use of the system.

The vaginal system described herein is further detailed with reference to the examples shown below. These examples are provided for the purpose of illustration only and the embodiments described herein should in no way be construed as being limited to these examples. Rather, the embodiments should be construed to encompass any and all variations which become evident as a result of the teachings provided herein.

EXAMPLES

Example 1: Condom Compatibility Testing

Five different types of condoms (three latex, one polyisoprene, and one polyurethane) were tested to determine if exposure to the vaginal ring system described herein would result in detrimental effects to the condom. Condom strength was measured using four different parameters: Force required for breakage (break force), percent condom elongation at breakage (percent elongation), pressure required to cause the condom to burst (burst pressure), and the condom's volume at burst (burst volume). A baseline was established for the analysis by measuring the four parameters of the condoms in their "as-received" condition with no exposure to heat, the ring system, or any lubricants (labeled "Baseline" in Table 1, below).

To test the compatibility of the vaginal system components with the condoms, an aqueous extract was prepared by placing 20 vaginal ring systems in a sufficient amount of water to test 20 condoms and agitating the resulting mixture for 24 hours. After the 24-hour period, the vaginal ring bodies were removed and the remaining extract was saturated with segesterone acetate and ethinyl estradiol. The amounts of segesterone acetate and ethinyl estradiol needed to ensure saturation were calculated by multiplying the solubilities of segesterone acetate and ethinyl estradiol in water at neutral pH (18.5 µg/mL and 11.0 µg/mL, respectively) by the volume of extract and adding an additional 20% of each agent.

Each type of condom was then covered with the saturated extract and conditioned at 40° C. for 1 hour at which time the four parameters described above were measured (labeled "Sample" in Table 1). Two controls were also included: one where each condom was subjected to the same preparation and conditioning using water in place of the saturated extract (labeled "Control" in Table 1), and one where each condom was subjected to the same preparation and conditioning using mineral oil in place of the saturated extract (labeled "Mineral Oil" in Table 1).

As shown in Tables 1 and 2, the parameters of each condom in the "Sample" category measured within 10% of condoms in the "Control" group, illustrating that exposure to the components of the vaginal ring system did not cause detrimental effects to the condoms. In contrast, condoms exposed to the mineral oil lubricant became significantly weaker.

TABLE 1

Change in Condom Strength After Exposure to Vaginal Ring System Components

| Condom Type | Exposure | Break Force in Newtons (N) and Standard Deviation (SD) | | Percent Elongation at Break (%) and Standard Deviation (SD) | | Burst Pressure in Kilopascals (kPa) and Standard Deviation (SD) | | Burst Volume in Liters (L) and Standard Deviation (SD) | |
|---|---|---|---|---|---|---|---|---|---|
| | | (N) | SD | (%) | SD | (kPa) | SD | (L) | SD |
| Trojan ® Enz ® Latex (non-Lubricated) | Baseline | 103.7 | 6.8 | 880.0 | 17.3 | 2.0 | 0.2 | 32.7 | 3.2 |
| | Control | 94.4 | 13.4 | 852.0 | 30.0 | 1.9 | 0.1 | 36.6 | 3.0 |
| | Mineral Oil | 4.7 | 1.1 | 326.0 | 85.0 | 0.9 | 17.7 | 0.1 | 9.8 |
| | Sample | 89.7 | 8.9 | 875.0 | 25.6 | 1.9 | 0.1 | 35.8 | 2.3 |
| LifeStyles ® Latex (non-Lubricated) | Baseline | 86.3 | 9.7 | 792.0 | 21.0 | 2.3 | 0.2 | 38.5 | 3.1 |
| | Control | 78.0 | 8.8 | 795.0 | 25.5 | 2.3 | 0.2 | 40.3 | 3.8 |
| | Mineral Oil | 12.0 | 5.0 | 542.0 | 138.1 | 1.1 | 0.2 | 27.6 | 6.7 |
| | Sample | 79.6 | 10.2 | 795.0 | 21.1 | 2.2 | 0.2 | 40.1 | 3.6 |
| Atlas ® Latex (non-Lubricated) | Baseline | 88.4 | 8.0 | 873.0 | 22.6 | 2.0 | 0.1 | 34.6 | 3.3 |
| | Control | 85.9 | 6.1 | 893.0 | 15.4 | 2.0 | 0.1 | 36.7 | 3.8 |
| | Mineral Oil | 12.3 | 5.0 | 556.0 | 174.4 | 0.8 | 0.1 | 17.4 | 8.3 |
| | Sample | 81.0 | 7.5 | 878.0 | 21.9 | 2.0 | 0.1 | 35.2 | 3.1 |
| LifeStyles ® Skyn ® Polyisoprene (Lubricated) | Baseline | 85.7 | 13.7 | 1033.0 | 31.5 | 1.8 | 0.1 | 46.8 | 2.8 |
| | Control | 80.9 | 10.5 | 1017.0 | 23.5 | 1.8 | 0.1 | 46.9 | 2.4 |
| | Mineral Oil | 24.6 | 9.6 | 781.0 | 131.5 | 0.7 | 0.0 | 13.9 | 2.1 |
| | Sample | 78.2 | 13.0 | 1013.0 | 29.5 | 1.7 | 0.2 | 45.3 | 3.8 |
| Trojan Supra ® Polyurethane (Lubricated) | Baseline | 46.1 | 10.8 | 539.0 | 17.1 | 9.8 | 0.9 | 7.6 | 0.6 |
| | Control | 44.7 | 7.8 | 532.0 | 13.9 | 9.3 | 0.9 | 8.7 | 0.9 |
| | Mineral Oil | 35.5 | 6.6 | 528.0 | 14.6 | 6.6 | 0.80 | 7.9 | 0.6 |
| | Sample | 45.6 | 12.1 | 537.0 | 20.2 | 9.1 | 0.6 | 8.6 | 0.6 |

TABLE 2

Percent Changes

| Condom Type | Break Force % Change (sample vs. control) | Elongation % Changes (sample vs. control) | Burst Pressure % Change (sample vs. control) | Burst Volume % Change (sample vs. control) |
|---|---|---|---|---|
| Trojan ® Enz ® Latex (non-Lubricated) | −5.0 | 2.7 | 0.0 | −2.3 |
| LifeStyles ® Latex (non-(Lubricated) | 2.1 | 0.0 | −2.4 | −0.5 |
| Atlas ® Latex (non-Lubricated) | −5.7 | −1.7 | −0.3 | −3.9 |
| LifeStyles ® Skyn ® Polyisoprene (Lubricated) | −3.3 | −0.4 | −3.9 | −3.4 |
| Trojan Supra ® Polyurethane (Lubricated) | 2.0 | 0.9 | −2.2 | −1.5 |

Percent change in Table 2 was calculated using the formula % change=100*(sample mean value−control mean value)/Control mean value Example 2: Pharmacodynamics Cardiac Electrophysiology The effect of SA on the QTc interval was evaluated in a Phase 1 randomized, placebo and positive controlled, double-blind, single-dose, three-period, crossover thorough QTc study in 44 healthy adult female subjects. At the single intravenous bolus dose which produces 4.5-fold the therapeutic serum concentrations of SA achieved with the vaginal system, SA did not prolong the QTc interval to any clinically relevant extent.

Example 3: Pharmacokinetics

Absorption

The pharmacokinetics (PK) of the vaginal system described herein were determined in 39 women who used the system for up to 13 product-use cycles. Following vaginal administration, SA and EE were absorbed into systemic circulation with median Tmax of about 2 hours in product-use cycle 1, product-use cycle 3, and product-use cycle 13. Concentrations of both components declined after Tmax and became more constant after 96 hours post-dose. Over subsequent product-use cycles, the peak serum concentrations of SA and EE declined. Serum concentration-time profiles of SA and EE for product-pse cycles 1, 3, and 13 of system use are provided in FIG. 1 and FIG. 2 with PK parameters summarized in Table 3 and Table 4.

TABLE 3

Mean (SD) PK Parameters for SA following Administration

| Cycle | $AUC_{0\text{-}21\ day}$ (ng * hr/mL) | $AUC_{0\text{-}1\ day}$ (ng * hr/mL) | $C_{max}$ (pg/mL) | $C_{avg}$ (pg/mL) |
|---|---|---|---|---|
| 1 | 96.2 (16.9) | 15 (3.2) | 1,147 (315) | 191 (34) |
| 3 | 65.9 (14.8) | 5 (1.6) | 363 (133) | 131 (29) |
| 13 | 47.2 (10.1) | 3.9 (1.4) | 294 (116) | 94 (20) |

TABLE 4

Mean (SD) PK Parameters for EE following Administration

| Cycle | $AUC_{0\text{-}21\ day}$ (ng * hr/mL) | $AUC_{0\text{-}1\ day}$ (ng * hr/mL) | $C_{max}$ (pg/mL) | $C_{avg}$ (pg/mL) |
|---|---|---|---|---|
| 1 | 22.2 (9.8) | 2.1 (0.7) | 129 (39) | 44 (19) |
| 3 | 14.7 (4.7) | 0.9 (0.4) | 60 (32) | 29 (9) |
| 13 | 9.6 (4.1) | 0.7 (0.3) | 39 (16) | 19 (8) |

The volume of distribution of SA is 19.6 L/kg. SA is approximately 95% bound to human serum proteins and has negligible binding affinity for sex hormone-binding globulin (SHBG). EE is highly protein bound but not specifically bound to serum albumin (98.5%) and induces an increase in the serum concentrations of SHBG.

Metabolism

In vitro data show that both SA and EE are metabolized by the cytochrome P450 (CYP) 3A4 isoenzyme. In human serum, two oxidative metabolites (5α-dihydro- and 17α-hydroxy-5αdihydro metabolites) constitute 50% of exposure relative to SA. Both metabolites are not considered as active metabolites with $EC_{50}$ to progesterone receptor 10-fold higher than that of SA. EE is primarily metabolized by aromatic hydroxylation, but a wide variety of hydroxylated and methylated metabolites are formed. These are present as free metabolites and as sulfate and glucuronide conjugates. The hydroxylated EE metabolites have weak estrogenic activity.

Excretion

The mean (SD) half-life of SA is 4.5 (3.4) hours. EE is known to be excreted in the urine and feces as glucuronide and sulfate conjugates, and it undergoes enterohepatic recirculation. The mean (SD) half-life of EE is 15.1 (7.5) hours.

The in vitro studies suggest that SA is unlikely to inhibit or induce CYP enzymes at the therapeutic dose.

Example 4: Clinical Trials

The clinical trials that evaluated the safety of the vaginal system described herein were obtained from three 13-cycle trials. One trial was conducted entirely in the U.S. (15 sites), and the other two were global studies that included 5 U.S. sites and 7 international sites (Australia, Brazil, Chile, Dominican Republic, Finland, Hungary, Sweden). All three trials were open label and enrolled healthy females, desiring contraception, 18 to 40 years of age. At about 50% enrollment, females with BMI>29 kg/m$^2$ were excluded due to the occurrence of two VTEs in this subgroup. In total, 2,308 females contributed 21,590 product-use cycles of exposure for safety evaluation and 999 completed 13 product-use cycles; there were 209 subjects with BMI>29 kg/m$^2$ who contributed 1,254 product-use cycles of exposure with 36 subjects completing 13 product-use cycles. The demographic profile for subjects was: mean age 26.7 years, mean BMI 24.1 (16.0-41.5) kg/m$^2$; 67% were from the U.S. The racial distribution was 71% Caucasian, 14% African American, 4% Asian, and 11% Other; 30% of the population was Hispanic.

The efficacy of the system was evaluated in two 1-year multicenter trials enrolling 2,265 females, age 18-40 years, who were healthy and sexually active with regular menstrual periods. The trials were conducted in the U.S., Dominican Republic, Brazil, Chile, Finland, Hungary, Sweden, and Australia, with 67.1% of females from the U.S. The racial/ethnic distribution was Caucasian (71.2%), African-American (14.1%), Asian (3.5%), other/multiple races (11.2%); 28.7% of the study population was Hispanic. The mean age was 26.7 years and the mean (range) BMI was 24.1 (16.0, 41.5) kg/m$^2$. At approximately 50% enrollment, women with BMI>29.0 kg/m$^2$ were no longer enrolled in the two trials and all women with a BMI>29.0 kg/m$^2$ were discontinued from the trials.

Based on pooled data from the two trials, 2,111 females ≤35 years of age completed 17,427 evaluable 28-day product-use cycles (cycles in which no back-up contraception was used). The pooled pregnancy rate, evaluated by the Pearl Index (PI), was 2.98 (95% Confidence Interval [2.13, 4.06]) per 100 woman-years of system use.

Return to fertility was assessed in 290 of the subjects in the two trials who either desired pregnancy or switched to a nonhormonal method after the trials, and all 290 subjects reported a return to fertility during the 6-month follow-up period (defined as a return of menses or pregnancy).

It is to be appreciated that the Detailed Description section, and not the Summary and Abstract sections, is intended to be used to interpret the claims. The Summary and Abstract sections may set forth one or more but not all exemplary embodiments of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

What is claimed is:

1. A method of providing birth control, the method comprising:
   (a) initially inserting into the vagina of a female of reproductive potential on either day 2, 3, 4, or 5 of the female's menstrual cycle, a vaginal system comprising:
   a silicone elastomer ring body, a first channel within the ring body, a second channel within the ring body, a first core disposed within the first channel, a second core disposed within the second channel, 103 mg of segesterone acetate, and 17.4 mg ethinyl estradiol, wherein the 103 mg of segesterone acetate is distributed throughout the first core and the second core; and wherein one of the first or second cores contains the 17.4 mg of ethinyl estradiol;
   wherein the system releases an average of approximately 0.15 mg/day of segesterone acetate and an average of approximately 0.013 mg/day of ethinyl estradiol in a 21-day first period as measured across thirteen 28-day product-use cycles; and
   wherein the initial insertion on day 2, 3, 4, or 5 is the first day of the 21-day first period;
   (b) removing the vaginal system from the female's vagina for more than two cumulative hours during the 21-day first period;
   (c) reinserting the vaginal system into the vagina of the female of reproductive potential following the removal of the vaginal system from the female's vagina in step (b) and employing a secondary contraception product that does not comprise estrogen for seven days after reinserting the vaginal system;
   (d) removing the vaginal system on the day following the end of the 21-day first period;
   (e) storing the removed vaginal system for a second period of between five and seven days including the removal date of step (d), wherein the 21-day first period and second period together comprise a product-use cycle; and
   (f) repeating steps (a), (d), and (e), and optionally repeating steps (b) and (c), for a total of up to thirteen product-use cycles including a first product-use cycle, wherein each initial insertion of step (a) is performed at approximately the same time of day as in a previous product-use cycle.

2. The method of claim 1, further comprising storing the vaginal system at room temperature when the vaginal system is removed from the vagina.

3. The method of claim 1, wherein removing the vaginal system from the female's vagina for more than two cumulative hours during the 21-day first period occurs in two or more instances on the same day, in two or more instances on consecutive or nonconsecutive days, or via a combination of occurrences on the same and different days.

4. The method of claim 1, wherein removing the vaginal system in step (b) comprises intentionally removing the system or expelling the system.

5. The method of claim 1, wherein the secondary contraception product that does not comprise estrogen is a male condom.

6. A method of providing birth control over the course of thirteen 28-day product-use-cycle, the method comprising:
   (a) initially inserting into the vagina of a female of reproductive potential on either day 2, 3, 4, or 5 of the female's menstrual cycle, a vaginal system comprising:
   a silicone elastomer ring body, a first channel within the ring body, a second channel within the ring body, a first core disposed within the first channel, a second core disposed within the second channel, 103 mg of segesterone acetate, and 17.4 mg ethinyl estradiol, wherein the 103 mg of segesterone acetate is distributed throughout the first core and the second core; and wherein one of the first or second cores contains the 17.4 mg of ethinyl estradiol;
   wherein the system releases an average of approximately 0.15 mg/day of segesterone acetate and an average of approximately 0.013 mg/day of ethinyl estradiol in a 21-day first period as measured across thirteen 28-day product-use cycles; and
   wherein the initial insertion on day 2, 3, 4, or 5 is the first day of the 21-day first period;
   (b) removing the vaginal system from the female's vagina for more than two cumulative hours during the 21-day first period;
   (c) storing the removed vaginal system for a second period of between five and seven days including the removal date of step (d), wherein the 21-day first period and second period together comprise a product-use cycle; and
   (d) repeating steps (a), (b), and (c) for a total of up to thirteen product-use cycles including a first product-use cycle, wherein each initial insertion of step (a) is performed at approximately the same time of day as in a previous product-use cycle;
   the method further comprising:
   (e) removing the vaginal system from the female's vagina for more than two cumulative hours during at least one of the 21-day first periods in any of the thirteen product-use cycles;
   (f) reinserting the vaginal system into the female's vagina following the removal of the vaginal system from the female's vagina in step (e); and
   (g) employing a secondary contraception product that does not comprise estrogen for seven days after reinserting the vaginal system into the female's vagina.

7. The method of claim 6, wherein removing the vaginal system from the female's vagina for more than two cumulative hours comprises intentionally, removing the vaginal system for more than two cumulative hours or unintentionally removing the vaginal system for more than two cumulative hours, or wherein removing the vaginal system for more than two cumulative hours comprises a combination of intentional and unintentional removals.

8. The method of claim 7, wherein unintentionally removing the vaginal system comprises expelling the vaginal system.

9. The method of claim 6, wherein the two cumulative hours out of the vagina are achieved via at least two instances wherein the vaginal system is removed from the vagina during the 21-day first period.

10. The method of claim 9, wherein the at least two instances take place on the same days or different days.

11. The method of claim 10, wherein the different days are consecutive different days or nonconsecutive different days.

\* \* \* \* \*